United States Patent
Petersen

(10) Patent No.: US 7,186,419 B2
(45) Date of Patent: Mar. 6, 2007

(54) POLYACRYLAMIDE HYDROGEL FOR ARTHRITIS

(75) Inventor: Jens Petersen, Birkerød (DK)

(73) Assignee: Contura SA, Montreux (CH)

( * ) Notice: Subject to any disclaimer, the term of this patent is extended or adjusted under 35 U.S.C. 154(b) by 237 days.

(21) Appl. No.: 09/938,668

(22) Filed: Aug. 27, 2001

(65) Prior Publication Data

US 2003/0065389 A1 Apr. 3, 2003

Related U.S. Application Data

(60) Provisional application No. 60/228,081, filed on Aug. 25, 2000.

(51) Int. Cl.
A61F 2/02 (2006.01)
A61K 31/785 (2006.01)
A61K 31/795 (2006.01)

(52) U.S. Cl. .................................. 424/423; 424/78.35

(58) Field of Classification Search ................ 424/423, 424/78.35; 523/114, 115

See application file for complete search history.

(56) References Cited

U.S. PATENT DOCUMENTS

| | | |
|---|---|---|
| 3,867,329 A | 2/1975 | Halpern et al. |
| 3,948,862 A | 4/1976 | Iwasyk |
| 4,074,039 A | 2/1978 | Lim et al. |
| 4,344,193 A | 8/1982 | Kenny |
| 4,502,161 A | 3/1985 | Wall |
| 4,535,131 A | 8/1985 | Handa et al. |
| 4,540,568 A | 9/1985 | Trager et al. |
| 4,657,656 A | 4/1987 | Ogawa |
| 4,713,434 A | 12/1987 | Sutterlin et al. |
| 4,746,551 A | 5/1988 | Allen et al. |
| 4,919,667 A | 4/1990 | Richmond |
| 5,135,480 A | 8/1992 | Bannon et al. |
| 5,171,322 A | 12/1992 | Kenny |
| 5,244,799 A | 9/1993 | Anderson |
| 5,306,404 A | 4/1994 | Notsu et al. |
| 5,344,451 A | 9/1994 | Dayton |
| 5,344,459 A | 9/1994 | Swartz |
| 5,482,719 A | 1/1996 | Guillet et al. |
| 5,589,104 A | 12/1996 | Bambeck |
| 5,652,274 A | 7/1997 | Martin |
| 5,658,329 A | 8/1997 | Purkait |
| 5,700,289 A | 12/1997 | Breitbart et al. |
| 5,798,096 A | 8/1998 | Pavlyk |
| 5,941,909 A | 8/1999 | Purkait |
| 6,252,016 B1 | 6/2001 | Wu et al. |
| 6,277,948 B1 | 8/2001 | Zahr |
| 6,335,028 B1 | 1/2002 | Vogel et al. |
| 6,486,213 B1 | 11/2002 | Chen et al. |
| RE38,913 E | 12/2005 | Pavlyk |
| 2005/0175704 A1 | 8/2005 | Petersen |

FOREIGN PATENT DOCUMENTS

| | | |
|---|---|---|
| CN | 1228447 | 9/1999 |
| EP | 0153672 B1 | 9/1985 |
| EP | 0153672 A2 | 9/1985 |
| EP | 0496067 A2 | 7/1992 |
| EP | 055119 A1 | 8/1993 |
| EP | 0727232 A2 | 8/1996 |
| EP | 0 727 232 A3 | 11/1996 |
| EP | 0742022 A1 | 11/1996 |
| EP | 742022 A1 * | 11/1996 |
| GB | 1317408 | 5/1973 |
| GB | 1320233 | 6/1973 |
| GB | 2114578 A | 6/1980 |
| GB | 2114578 A | 5/1981 |
| RU | 1697756 A1 | 6/1988 |
| RU | 1831709 | 7/1993 |
| RU | 2034465 | 5/1995 |
| RU | 2148957 | 2/1998 |
| RU | 2127129 | 3/1999 |
| RU | 2148957 | 5/2000 |
| SU | 1608193 | 11/1990 |
| SU | 1687291 | 10/1991 |
| WO | WO 81/01290 | 5/1981 |
| WO | WO 89/07455 | 8/1989 |
| WO | 96/04943 | 2/1996 |
| WO | WO 96/25129 | 8/1996 |
| WO | WO 99/10021 | 3/1999 |
| WO | 00/31148 | 6/2000 |
| WO | WO 00/59411 | 10/2000 |
| WO | WO 00/78356 | 12/2000 |
| WO | 01/38402 | 5/2001 |
| WO | 01/42312 A1 | 6/2001 |
| WO | 01/49336 A1 | 7/2001 |
| WO | WO 01/49336 A1 | 7/2001 |

OTHER PUBLICATIONS

Jarosova et al, analysis of Clinical and Laboratory Data in Group of Patients wih Juvenile Idiopathic Arthritis, Ceska Revmatologie, (2002), 10/2 (65–70).*

Gebauer et al, Gonoarthritis due to *Salmonella enteritidis* in a patient with systemic lupus erythematosus, Klinische Padiatrie, (Sep.–Oct. 2002) 214 (5) 319–23.*

U.S. Appl. No. 09/938,667, filed Aug. 27, 2001, Jens Petersen.

U.S. Appl. No. 09/938,669, filed Aug. 27, 2001, Jens Petersen.

U.S. Appl. No. 09/938,670, filed Aug. 27, 2001, Jens Petersen et al.

International Search Report dated Jan. 31, 2002, for Application PCT/DK01/00565, Filed Aug. 25, 2001.

(Continued)

Primary Examiner—Carlos A. Azpuru
(74) Attorney, Agent, or Firm—Hunton & Williams LLP

(57) ABSTRACT

A hydrogel for use as a prosthetic device for supplementing, augmenting or replacing cartilage in the intra-articular cavity of a joint and for treatment or prevention of arthritis. The hydrogel may be a polyacrylamide hydrogel obtained by combining acrylamide and methylene bis-acrylamide. A prosthetic device comprising the polyacrylamide hydrogel is also disclosed.

14 Claims, No Drawings

OTHER PUBLICATIONS

N.A. Peppas, 1986, *Hydrogels in Medicine and Pharmacy*, CRC Press, vol. I, pp. 2–6; 96–97.

RU, Lic. Reg. No. 94, May 20, 1994, Russion Fed, Irkutsk Region, License to Medical Insurance of Citizens in the RSFSR Act.

J.E. Gomez, and G.B. Thurston, Comparsions of the oscillatory shear viscoelasticity and composition of pathological synovial fluids, Biorheology 30, 409–427 (1993).

U.S. Appl. No. 11/469,213, filed Aug. 31, 2006, Petersen.

Ministry of Public Health of Ukraine, Kiev Research Institute of Hematology and Blood Transfusion, Report dated Feb. 29, 1993.

Interfall's Biocompatible Hydrogel, Doctors's Information (Feb. 22, 2006) (citing U.S. Appl. No. 5,798,096) at http://www.bpg.bg/interfall/EB005140106biocompatible_gel1.htm.

* cited by examiner

POLYACRYLAMIDE HYDROGEL FOR ARTHRITIS

REFERENCE TO PRIOR APPLICATION

This application claims priority under 35 U.S.C. § 119(e) from provisional application Ser. No. 60/228,081, filed Aug. 25, 2000, which is incorporated herein by reference.

FIELD OF INVENTION

The use of a hydrogel comprising 0.5 to 25% polyacrylamide by weight as a prosthetic device for the alleviation or prevention of pain in joints, such as weight bearing joints, is provides an advantageous treatment of arthritis. The hydrogel provides lubrication and support to existing cartilage in the intra-articular cavity of the joint.

BACKGROUND OF THE INVENTION

Arthritis is a degenerative condition which, when affecting the weight bearing joints such as the hip and knee joints, results in pain and hampered mobility. Arthritis may affect all joints. Degradation of articular and meniscal cartilage may result in damage to the surfaces separated by the cartilage and correspondingly to pain. Ageing is a primary cause of the degradation of the cartilage. The degradation may also result from, for example, congenital predisposition or trauma, such as repeated articulation of the joint.

Arthritis has been treated traditionally with physiotherapy and more invasive treatments such as orthopaedic surgery and the introduction of artificial joint components. Non-steroidal anti-inflammatory agents have been used with some success but these agents may counterproductively hamper proteoglycan synthesis in collagen and cartilage as well as have undesirable side effects. Cortisone injections also weaken articular cartilage with time.

Soft compliant materials used to replace the cartilage have been developed to absorb the load on the joint and to distribute the load evenly. U.S. Pat. No. 4,344,193 discloses silicone rubber as a prosthetic device. One difficulty with these devices is securing the devices in place and various anchoring systems have been developed (U.S. Pat. No. 5,171,322; U.S. Pat. No. 4,502,161; U.S. Pat. No. 4,919,667).

Other prosthetic devices, such as in U.S. Pat. No. 5,344,459, are inflatable. The Macintosh knee is a hard prosthetic which is painful to use.

WO 00/78356 discloses an injectable composition for promoting bone and/or cartilage growth comprising hyaluronic acid cross-linked to sulfated polysaccharides.

WO 96/25129 discloses a prosthesis for joints in hands and feet comprising a biocompatible material such as a mixture of biocompatible resin and plastics. Specific materials mentioned include polymethyl methacrylate polymer. The prosthesis is implanted into the joint.

WO 00/59411 discloses a surgically implanted knee prosthesis wherein the load distribution device is constructed of material comprising a thermoset polymer or thermoplastic polymer.

Hyaluronates and hyaluronic acids have been used for prosthetics and administered by injection into the intra-articular cavity of knees for the long-term relief of pain and improvement on the function of the knee joint. It has adequate viscosity and elasticity but has been prone to sheering due to mechanical stress and is biodegradable and has faced resorption problems.

There is the need in the art for additional materials for use as an artificial cartilage such as in weight-bearing joints. The present invention is directed to a material and prosthetic device for use in the treatment of arthritis and to supplement or replace cartilage.

SUMMARY OF THE INVENTION

One object of the invention is to provide a polyacrylamide hydrogel for use as a prosthetic device for supplementing, augmenting or replacing cartilage in the intra-articular cavity of a joint. The soft material has at least two advantageous features in that the material is firstly both biocompatible and biostable; and secondly, the material is mechanically resilient and does not bead, tear, shred or disintegrate readily upon mechanical stress. The material may be injected or implanted and manipulated so as to distribute the support provided by the material uniformly or according to the needs of the patient. The hydrogel also provides lubrication to the joint and the pre-existing cartilage.

A central object of the invention is to provide a hydrogel for use in the treatment or prevention of arthritis, said hydrogel obtainable by combining acrylamide and methylene bis-acrylamide in amounts so as to give about 0.5 to 25% by weight polyacrylamide, based on the total weight of the hydrogel; radical initiation; and washing with pyrogen-free water or saline solution.

A further aspect of the invention relates to the use of a hydrogel comprising about 0.5 to 25% by weight polyacrylamide, based on the total weight of the hydrogel, for the preparation of an endoprosthesis for alleviation or prevention of symptoms associated with arthritis.

Furthermore, providing a method of treating or preventing arthritis comprising administering a hydrogel to a mammal said hydrogel comprising 0.5 to 25% by weight polyacrylamide, based on the total weight of the hydrogel is further object of the invention.

Another aspect of the invention relates to a prosthetic device for the treatment of arthritis, wherein the device comprises a polyacrylamide hydrogel comprising 0.5 to 25% by weight polyacrylamide, based on the total weight of the hydrogel, said device administered to the intra-articular cavity of joint. Alternatively defined, the prosthetic device of the invention is for augmenting or replacing cartilage in the intra-articular cavity of a joint, said device comprises a polyacrylamide hydrogel comprising 0.5 to 25% by weight polyacrylamide, based on the total weight of the hydrogel.

GENERAL DESCRIPTION OF THE INVENTION

The polyacrylamide hydrogel is resistant to biological degradation and is not permeable through biological membranes. The polyacrylamide hydrogel of the invention is fully biocompatible (according to ISO standard test ISO-10993). The polyacrylamide hydrogel does not have cytotoxic effect on human fibroblasts, is non-toxic, non-carcinogenic, non-allergenic, non-mutagenic, and resistant to enzymatic and microbiological degradation. Furthermore, the polymer is not water-soluble. Notable for the invention, the polymer is resilient to mechanical stress.

The hydrogel of the present invention is for use in the in the treatment or prevention of arthritis, the hydrogel obtainable by combining acrylamide and methylene bis-acrylamide radical initiation; and washing with pyrogen-free water or saline solution, the combining being in amounts and the washing being such that to give about 0.5 to 25% by weight polyacrylamide, based on the total weight of the hydrogel. The hydrogel obtained has been shown by the present investigators to be both biostable and biocompatible, and is not resorbed by the body. Moreover, the present investigators have demonstrated the hydrogel to be resilient to mechanical stress.

Typically, the hydrogel of the invention is obtained by combining acrylamide and methylene bis-acrylamide is in a molar ratio of 150:1 to 1000:1. The conditions for obtaining the hydrogel may be modified according to, for instance, the nature of the joint into which the hydrogel is intended to be injected. The desired rheologically properties, such as elasticity and viscosity may be controlled at least in part by the solid weight content of the hydrogel. The hydrogel of the invention comprises about 0.5 to 25% by weight polyacrylamide, based on the total weight of the hydrogel. In suitable embodiments of the invention, the hydrogel comprises less than 15% by weight polyacrylamide, based on the total weight of the hydrogel, preferably less 10%, more preferably less than 7.5%, even more preferably less than 5%, most preferably less than 3.5% by weight polyacrylamide, based on the total weight of the hydrogel.

Given the hydrogel of the invention is directed for use as an endoprosthesis, it must be stable. Typically, such as for reasons of increased stability, the hydrogel comprises at least 1% by weight polyacrylamide, based on the total weight of the hydrogel, preferably at least 1.5%, such as 1.6% by weight polyacrylamide, based on the total weight of the hydrogel. In suitable embodiments, the hydrogel of the present invention has a solid weight content of at least 1.5 and less than 3.5% by weight polyacrylamide, based on the total weight of the hydrogel such as 1.5, 1.6, 1.7 1.8, 1.9, 2.0, 2.1, 2.2, 2.3, 2.4, 2.5, 2.6, 2.7, 2.8, 2.9, 3.0, 3.1, 3.2, 3.3, and 3.4% polyacrylamide, based on the total weight of the hydrogel.

The combining involves the combining of the component reagents acrylamide and methylene bis-acrylamide, typically degassed and typically in a manner to minimise operator contact. The reagent components may be optionally previously combined to form an inert mixture. An inert mixture is one wherein no chemical reaction proceeds among the component reagents. The combining involves combining acrylamide, methylene-bis-acrylamide, and a radical initiator component. In a suitable embodiment, an inert premixture of acrylamide, methylene-bis-acrylamide (the cross-linker) and TEMED is combined with an AMPS initiator solution. However, the components may be combined as singularities or as alternative plural premixtures.

Acrylamide and methylene-bis-acrylamide are suitably combined in a molar ratio of about 100:1 to 1000:1, typically about 150:1 to 900:1, preferably about 175:1 to 800:1, more preferably about 200:1 to 600:1, most preferably from 250:1 to 500:1. As shown in Tables 2 and 3, hydrogels of differing solid-weight content and rheological properties may be controllably prepared. The hydrogel having the desired rheological characteristics has been obtained by combining acrylamide and methylene-bis-acrylamide in a ratio of about 250:1, about 260:1, about 270:1, about 280:1, about 290:1, about about 300:1, about 310:1, about 320:1, about 330:1, about 340:1, about 350:1, about 360:1, about 370:1, about 380:1, about 390:1, about 400:1, about 410:1, about 420:1, about 430:1, about 440:1, about 450:1, about 460:1, about 470:1, about 480:1, about 490:1 and about 500:1.

As can also be seen from Tables 2 and 3, the relative amount of monomer (acrylamide and methylene-bis-acrylamide) is fairly constant from formulation to formulation in relation to TEMED. Thus, in a preferred embodiment of the method of the invention, the ratio of monomers to TEMED is relatively constant from batch to batch and not used to regulate the rheological properties of the polymer. In the embodiment wherein the polymer is polyacrylamide, the ratio of the monomers acrylamide and methylene-bis-acrylamide to TEMED is about 100:1 to 700:1, such as 200:1 to 600:1, typically 200:1 to 500:1, preferably 200:1 to 400:1, most preferably 200:1 to 350:1.

Similarly, the relative amount of monomer (acrylamide and methylene-bis-acrylamide) is fairly constant from formulation to formulation in relation to the amount of initiator. Thus, in a preferred embodiment of the method of the invention, the ratio of monomers to initiator is relatively constant from batch to batch and not used to regulate the rheological properties of the polymer. In the embodiment wherein the polymer is polyacrylamide, the ratio of the monomers acrylamide and methylene-bis-acrylamide to initiator is about 100:1 to 700:1, such as 200:1 to 600:1, typically 200:1 to 500:1, preferably 200:1 to 400:1, most preferably 200:1 to 350:1.

The viscosity of the hydrogel is suitably such that it may be injected. In a typical embodiment, the hydrogel has a complex viscosity of about 2 to 20 Pa s, such as about 3 to 18 Pa s, preferably about 3 to 15 Pa s, most preferably about 2 to 13 Pa s.

The hydrogel of the invention is substantially free of materials which contribute to the solid weight content other than the acrylamide, methylene-bis-acrylamide and residual amounts (if any) of the initiators. The hydrogel is substantially free of any other polymeric content. The hydrogel further comprises at least 75% by weight pyrogen-free water or saline solution, preferably pyrogen-free water. In a suitable embodiment of the invention, the hydrogel comprises at least 80% by weight pyrogen-free water or saline solution, preferably at least 85%, more preferably at least 90%, even more preferably at least 95% by weight pyrogen-free water or saline solution.

A suitable saline solution has an osmolarity similar to that of interstitial fluid. Suitable saline solutions include but are not limited to the group selected from 0.25–1% aqueous sodium chloride, a Ringer-Lockart solution, an Earle solution, a Hanks solution, an Eagle medium, a 0.25–1% glucose solution, a potassium chloride solution, and a calcium chloride solution. In a preferred embodiment, the saline solution is a 0.8–1% aqueous sodium chloride solution, such as a 0.8, 0.9 or 1% aqueous sodium chloride solution, most preferably about 0.9% aqueous sodium chloride.

As will be obvious to the person skilled in the art, in the embodiment wherein saline solution is used either for the preparation of the gel and/or for the washing of the gel, the solid-weight content of the gel will be higher than the contribution made by the polyacrylamide, but typically not more than an additional 1%.

In a particularly suitable embodiment of the invention, the hydrogel comprises about 2.5% by weight polyacrylamide, based on the total weight of the hydrogel and about 97.5% pyrogen-free water.

Pyrogen-free water or saline solution is used for the washing process. The washing process serves, in part, to remove all but trace amounts of the monomers acrylamide and N,N'-methylene-bis-acrylamide. These monomers are toxic to the patient as well as detrimental to the stability of the hydrogel. The washing process is preferably such that the concentrations of the monomers acrylamide and N,N'-methylene-bis-acrylamide are below 50 ppm, more preferably below 40 ppm, such as below 30 ppm, most preferably below 20 ppm, typically below 10 ppm, particularly preferably below 5 ppm.

In an alternative embodiment of the invention, the hydrogel has a more solid consistency such that it is implantable into a joint cavity. In such embodiments wherein the hydrogel has a solid consistency, the hydrogel may be surface-modified so as to decrease slippage from the area it was implanted. Surface modification may be chemical or physical in nature. Hydrogels of with a solid weight content have been prepared which are solid like and suitable for implantation rather than injection and very amenable to surface modification.

In the embodiment wherein the hydrogel is implantable, the viscosity of the solid sample is obviously very high. In the embodiment wherein the hydrogel is implantable, the hydrogel has a complex viscosity of about 20 to 1500 Pa s, typically 20 to 1000 Pa s.

In the embodiment, wherein the hydrogel is implantable and furthermore surface-modified, in the event that the hydrogel is surface modified by chemical treatment, it is anticipated that the chemical treatment will account for less than 1% of the weight of the hydrogel based on the total weight of the hydrogel. Chemical treatment may comprise of a surface coating agent or an agent which acts topically to chemically modify the polyacrylamide at the surface of the hydrogel.

The hydrogel of the invention is used for the preparation of an endoprosthesis to be inserted into the intra-articular cavity of joint. The gel is intended for use as a prosthetic device in the treatment of arthritis. The prosthetic device of the invention comprises a polyacrylamide hydrogel comprising 0.5 to 25% by weight polyacrylamide, based on the total weight of the hydrogel and is administered to the intra-articular cavity of joint.

The prosthetic device may comprise any embodiment of the hydrogel as described supra. Accordingly, the device is used for augmenting or replacing cartilage in the intra-articular cavity of a joint, said device comprises a polyacrylamide hydrogel comprising 0.5 to 25% by weight polyacrylamide, based on the total weight of the hydrogel. In the prosthetic device of the invention the hydrogel typically further comprises at least 75% by weight pyrogen-free water or saline solution, preferably pyrogen-free water. It may be administered by implantation or injection into the intra-articular cavity of a joint. Preferably, the device is injected.

The device may have a viscosity such that it may be injected. In an embodiment wherein the hydrogel is injected, the hydrogel has a complex viscosity of about 2 to 25 Pa s, such as about 3 to 20 Pa s, preferably about 3 to 18 Pa s, most preferably about 3 to 15 Pa s, such as 3, 4, 5, 6, 7, 8, 9, 10, 11, 12, 13, 14, and 15 Pa s.

Particularly in the embodiment wherein the hydrogel is injected into a weight-bearing joint, the elasticity of the hydrogel and device is of great relevance. In a preferred embodiment, the hydrogel of the invention has an elasticity modulus of about 1 to 200 Pa, such as about 2 to 175 Pa, typically about 5 to 150 Pa, such as 10 to 100 Pa.

The elasticity modulus of the prosthetic device and the complex viscosity are typically related by a factor of 5.8 to 6.4. The present invention thus provides for a hydrogel with the advantageous combined features of a viscosity suitable for being injectable and of an elasticity to supplement weight-bearing capacity. In a combination of preferred embodiments, the hydrogel has a complex viscosity less than 25 Pa s and an elasticity modulus less than 200 Pa, preferably having a complex viscosity less than 15 Pa s and an elasticity modulus less than 100 Pa.

Example 1, Tables 1, 2 and 3, illustrate appropriate conditions for preparing the illustrative examples of hydrogels. As can be seen, within the preferred combined embodiment of a viscosity of less than 25 Pa s and an elasticity modulus of less than 200 Pa, such as a complex viscosity of less than 15 Pa s and an elasticity of less than 100, the hydrogel may have an array of dry-weight content percentages.

Furthermore, still within the preferred combined embodiment of a viscosity of less than 25 Pa s and an elasticity less than 200 Pa, such as having a complex viscosity less than 15 Pa s and an elasticity less than 100, the hydrogel is obtainable by combining acrylamide and methylene-bis-acrylamide in a molar ratio of about 275 to 1000, typically 300 to 800, preferably in a ratio of about 300 to 500.

The hydrogel of the invention is resilient to mechanical stress as well as providing lubrication within the joint. This mimics the combination of naturally occurring cartilage and synovial fluid in the joint. Synovial fluid is produced by the synovial membrane and forms in the interface with both the synovium and the articular cartilage. Its function is nutrition of the cartilage, lubrication, load bearing and shock absorption (see Gomez and Thurston, *Biorheology* 30, 409–427 (1993)). Synovial liquid is a solution of a very sophisticated polymer complex made of the linear hyaluronic acid backbone having protein branches and has an elasticity modulus G' of 60 Pa and a complex viscosity of about 1–10 Pa s. Certain embodiments of the hydrogel of the invention typically has very similar elasticity modulus and viscosity.

Synovial liquid, being a fluid, has a very long relaxation time (about 100 sec). The relaxation time is defined as the time required for the stress to decay to 37% of its initial value in a stress relaxation experiment. This long relaxation time implies that for fast movements (when the stress is applied rapidly), it responds as a very elastic material, whereas at low speed stresses it behaves like a lubricating oil. Low viscosity formulations of the hydrogel of the invention are fluid-like, such as when homogenised, and as fluids, have the very long relaxation time and the fluid like properties of synovial liquid. The present invention thus provides for an excellent alternative to known technologies for replacing synovial liquid, such as injections with isotonic (NaCl) water which lasts for only 1–3 days, or injection with solutions of hyaluronic acid, which faces resorption problems.

As stated, in embodiments wherein the hydrogel is a low viscosity formulation, the hydrogel attempts to mimic, at least in part, the features of synovial liquid. In embodiments where the hydrogel is of higher viscosity formulation, such as a viscosity above 10 Pa s, such as above 15 Pa s, the hydrogel mimics more the combined features of synovial liquid and cartilage in that the hydrogels are more elastic materials with infinite relaxation times.

In terms of resilience to mechanical stress, the hydrogel of the invention has demonstrated complete full resilient behaviour. Moreover, the elastic feature of the hydrogel allows it to return to its start position when the stress is released in creep experiments.

The device may be administered into an array of intra-articular cavities where said joint or cartilage present in said joint may need increased lubrication, increased weight bearing capacity, or increased protection of the opposing bones of the joint, such as but not limited to the group comprising the knee joint; hip joint; the elbow, the metacarpal-phalangeal and interphalangeal joints in hands and feet.

In the administration of the device to the patient, the adequate placing and position of the hydrogel is of great relevance. To assist in the positioning of the gel, visualisation of the location of the device is useful to the individual performing the procedure. It may be advantageous, such as in the embodiment wherein the device is administered by injection to visualise the device in order to establish its position and the amount required. Visualisation of the hydrogel during administration may be facilitated by radio-labelling of the hydrogel. Thus, in one interesting embodiment, the hydrogel is radio-labelled.

As stated, surface treatment of the hydrogel may assist device to be held in place within the joint cavity. However, in the embodiment of an injectable hydrogel, the device may be held by the bone tissue which defines the boundaries of the cavity into which the gel was injected.

As also stated, one aspect of the invention relates to the use of a hydrogel comprising about 0.5 to 25% by weight polyacrylamide, based on the total weight of the hydrogel, for the preparation of an endoprosthesis for alleviation or prevention of symptoms associated with arthritis. Correspondingly, the method of the invention may be defined as a method of treating or preventing arthritis comprising administering a hydrogel to a mammal said hydrogel comprising 0.5 to 25% by weight polyacrylamide, based on the total weight of the hydrogel. The method comprises the use of the hydrogel as defined supra and to the use of the prosthetic device as defined supra.

The method may comprise a first series or treatment session of injections or implantations followed by an analysis, evaluation or trial of the degree of assistance provided by the device and followed by further series or treatment sessions if required. In the embodiment wherein the joint required primarily increased weight bearing capacity, the elasticity or support provided by the device may diminish with time. However, one advantage of the method of the invention is that an injectable formulation of the prosthetic device may be administered to supplement the existing device. This procedure may be repeated as often as required by the patient to alleviate the pain associated with the condition. Similarly, in the event that the device was administered primarily to increase lubrication in the joint, and that the lubrication capacity of the device has diminished with time, the method of the invention, such as by simple injection may be repeated as required.

EXAMPLES

Example 1

Preparation of Hydrogel

The gel is a polyacrylamide gel manufactured by a polymerisation of the monomers of acrylamide and N,N'-methylene-bis-acrylamide. The finished product may have different viscosities.

The hydrogel has the empirical formula $[C_3H_5NO]_x$ $[C_7H_{10}N_2O_2]_y$, and the structural formula as shown in Figure 1

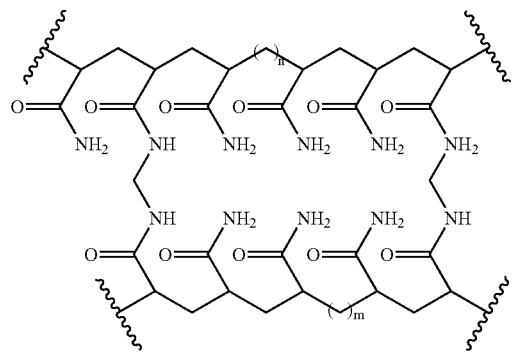

FIG. 1

The hydrogel typically contains approximately 95% water. The concentration of the monomers acrylamide and N,N'-methylene-bis-acrylamide has been shown to be less than 10 ppm and is adequate for the desired stability of the final product, often less than 5 ppm.

The finished product must conform with respect to pH, absence of heavy metals, refractive index, stability, absence of pyrogens, and must be sterile, practically inert, and be substantially free of monomers.

Preparation 1.1

The synthetic preparation suitably involves the following operations:
1. Two mixtures, A1 and A2, are prepared. A1 comprises water, acrylamide, N,N'-methylene-bis-acrylamide, N,N, N', N'-tetramethylene-ethylene-diamine (TEMED). A2 comprises water and ammonium persulphate;
2. The two mixtures are combined in the following ratio: 1990 mL of A1 and 10 mL of A2 and kept at 45° C. and degassed with nitrogen for 20 seconds;
3. The reaction mixture is cast into several 100 mL beakers;
4. Polymerisation is allowed to occur for 0.5 to 1.5 hours;
5. The gel is demolded;
6. Residual monomers are extracted and with equilibration in WFI water for 92 hours, changing the water several times, typically 8 times during the 92 hours;
7. The purified gels are homogenised by grinding with an vertically oscillating grid;
8. The syringe is filled with the homogenised gel material;
9. Autoclavation of the syringe A typical method for preparing the hydrogel may be summarised as:

Preparation 1.2

Process summary: The gel is prepared by mixing an aqueous monomer solution of acrylamide and N,N'-methylene-bis-acrylamide as cross-linker with N,N,N', N'-tetramethylene ethylene diamine (TMED) as co-initiator and ammoniumpersulfate (APS) as free-radical initiator (redox-system). By degassing a bulk solution with nitrogen polymerisation starts. After final polymerisation the gel transferred into a washing tank with net trays onto which the gel is placed. During water washing the gel swells and monomer residues are extracted. The swollen gel is fed and evacuated in a filling unit having the gel delivered in a syringe, which is autoclaved.

Two alternate formulations have been prepared, a lower- and a higher-end viscosity formulation. Both formulations have a solid weight content of less than 3.5% and a complex viscosity in the range of 2 to 50 Pa s, typically between 3 and 20 Pa s.

TABLE 1

| Chemical constituent | lower end viscosity | higher end viscosity |
| --- | --- | --- |
| acrylamide | 502 g | 547 g |
| N,N'-methylene-bis-acrylamide | 2.2 g | 4.6 g |
| TMED | 3.0 g | 2.6 g |
| APS | 5.4 g | 5.0 g |
| Non-pyrogenic water | Add 10 liter | Add 10 liter |

The above are typical preparations of the hydrogel and may be adjusted within certain ranges.

Preparation 1.3

Polyacrylamide Formulations from Inline Cross-linking Process

A particularly interesting method of preparing the hydrogels of the invention involves an inline cross-linking process. Two individual and eventually degassed flows, one being a pre-mix of acrylic amide, bis-methylene acrylamide (the cross-linker) and TEMED, the other being the AMPS initiator solution, are pumped into a static mixer for mixing, chemical initiation and subsequent extrusion downstream into a pipe reactor made of Teflon or steel in which the polymerisation occurs. Washing of the gel is simplified due to high surface area of gel from reactor.

By selecting monomer, cross-linker and initiator concentrations and their relative molar ratios, and by regulating the two flow rates and the polymerisation temperatures, it is possible to produce gels that are varying in degree of crosslinking and in solids content.

Preparation 1.4

The reagents were combined in ratios described in Tables 2, 3 and 4, and washed as described in the Tables (with pyrogen-free water unless indicated otherwise) to give low, medium, and high viscosity formulations. Hydrogels with solid weight contents between 0.5 and 25% polyacrylamide were prepared.

TABLE 2

Process parameters and features of resulting gel: low viscosity formulations

| | Iv1 | Iv2 | Iv3 | Iv4 | Iv5 | Iv6 | Iv7[d] | Iv8[e] |
| --- | --- | --- | --- | --- | --- | --- | --- | --- |
| washing time (hrs) | a) | 19.5 | 73.75 | 92 | 94.3 | 72.8 | 93.6 | 93.9 |
| dry matter[i] (%) | 2.55 | 2.08 | 2.63 | 2.87 | 2.89 | 3.15 | 3.68 | 3.17 |
| | | 2.36 | 2.58 | 2.67 | 2.82 | 2.90 | 3.57 | 3.52 |
| | | | 2.09 | | | | | |
| molar ratio AM:bisAM | b) | 976 | 700 | 488 | 366 | 3239 | 488 | 488 |
| molar ratio AM + BISAM: TEMED | 252 | 252 | 253 | 251 | 252 | 249 | 252 | 252 |
| molar ratio AM + BISAM: APS | 298 | 299 | 298 | 298 | 298 | 299 | 298 | 298 |
| residual monomer in ppm | c) | 89 | 5 | 2.97 | 2 | 5 | 1.4 | 0.97 |
| elasticity G' in Pa | 0.16 | 5.23 | 14.3 | 26.6 | 57.05 | 71.7 | 39.2 | 28.5 |
| | | | 20.1 | | | | | |
| viscosity in Pa s | .045 | .88 | 2.35 | 4.37 | 9.1 | 11.5 | 6.29 | 4.55 |
| | | | 3.30 | | | | | |
| gelation time (min) | liquid | highly viscous liquid | 12 | 2 | 2 | 2 | 2.5 | 2.5 |

| | Iv9 | Iv10 | Iv11 | Iv11 | Iv12 |
| --- | --- | --- | --- | --- | --- |
| washing time (hrs) | 121 | 96.4 | | | |
| dry matter (%) | 2.18 | (5.10)[f] | (10.2)[f] | (10.1)[f] | (20.2)[f] |
| molar ratio AM:bisAM | 701 | 701 | 488 | 488 | 488 |
| molar ratio AM + BISAM: TEMED | 252 | 252 | 252 | 504 | 2016 |
| molar ratio AM + BISAM: APS | 298 | 298 | 298 | 596 | 2385 |
| residual monomer in ppm | | 0.97 | | | |
| elasticity G' in Pa | 28.5 | 11.1 | (911)[g] | (1240)[g] | (9460)[g] |
| viscosity in Pa s | 4.55 | 1.8 | (145)[g] | (197)[g] | (1505)[g] |

TABLE 2-continued

Process parameters and features of resulting gel: low viscosity formulations

| | | | | |
|---|---|---|---|---|
| gelation time (min) | 3.17 | 0.00 | 1.21 | 3.5[h] | a) material was liquid so washing was a dilution
b) infinite
c) since washing was not an extraction but a dilution, the residual monomer was merely decreased by the dilution factor (508 ppm to 254 ppm).
[d] casting and washing done using 0.9% NaCl aqueous solution
[e] casting with water; washing done using 0.9% NaCl aqueous solution
[f] pre-wash values - washing typically reduces value by 30–55%
[g] pre-wash values - washing typically reduces value by 20–40%
[h] highly notch sensitive
[i] variations in values may be due to measurement performance techniques or to location in the batch from which sample was taken

TABLE 3

Process parameters and features of resulting gel: medium viscosity formulations

| | mv1 | mv2 | mv3 | mv4 | mv5 |
|---|---|---|---|---|---|
| washing time (hrs) | 97 | 211.5 | 96 | 94.8 | 90.3 |
| dry matter (%) | 3.14 | 2.49 | 3.25 | 3.29 | 3.22 |
| molar ratio AM:bisAM | 310 | 310 | 290 | 289 | 289 |
| molar ratio AM + BISAM: TEMED | 252 | 252 | 252 | 251 | 252 |
| molar ratio AM + BISAM: APS | 299 | 299 | 299 | 299 | 299 |
| residual monomer in ppm | 1.6 | | 1.5 | | |
| elasticity G' in Pa | 108.5 | | 129 | 133.5 | |
| viscosity in Pa s | 17.4 | | 20.6 | 21.30 | |
| gelation time (min) | 2.5 | 2.5 | 2.18 | | |

TABLE 4

Process parameters and features of resulting gel: high viscosity formulations

| | hv1 | hv2 | hv3 | hv4 | hv5 |
|---|---|---|---|---|---|
| washing time (hrs) | 119.5 | 516 | 122 | 95.5 | 116.7 |
| dry matter (%) | 3.47 | 2.5 | 3.56 | 3.83 | 3.42 |
| molar ratio AM:bisAM | 260 | 260 | 260 | 260 | 260 |
| molar ratio AM + BISAM: TEMED | 315 | 315 | 604 | 313 | 314 |
| molar ratio AM + BISAM: APS | 376 | 376 | 755 | 375 | 376 |
| residual monomer in ppm | 0.2 | | | | |
| elasticity G' in Pa | 343 | 274 | | 314.5 | |
| viscosity in Pa s | 54.7 | 43.65 | | 50.1 | |
| gelation time (min) | 2.18 | 2.18 | 7.5 | | |

What is claimed is:

1. A method for replacing, mimicking or augmenting a function of cartilage, synovial fluid or both comprising administering an endoprosthesis to a joint in a mammal, wherein said endoprosthesis comprises a hydrogel, said hydrogel comprising 0.5% to 25% by weight polyacrylamide, based on the total weight of the hydrogel.

2. The method according to claim 1, wherein the hydrogel is obtained by a process comprising combining acrylamide and methylene bis-acrylamide in a molar ratio of 150:1 to 1000:1.

3. The method according to claim 1, wherein the hydrogel comprises less than 15% by weight polyacrylamide, based on the total weight of the hydrogel.

4. The method according to claim 3, wherein the hydrogel comprises at least 1% by weight polyacrylamide, based on the total weight of the hydrogel.

5. The method according to claim 1, wherein the hydrogel has a complex viscosity of about 2 to 25 Pa s.

6. The method according to claim 1, wherein the hydrogel further comprises at least 75% by weight pyrogen-free water or saline solution.

7. The method according to claim 1, wherein the hydrogel comprises at least 80% by weight pyrogen-free water or saline solution.

8. The method according to claim 1, wherein the administering comprises injecting the hydrogel into an intra-articular cavity of the joint.

9. The method according to claim 1, wherein the hydrogel is radio-labeled and the administering may be monitored by visualization.

10. The method according to claim 8, further comprising administering hydrogel injections to excessively stressed areas of the intra-articular cavity.

11. The method according to claim 1, wherein the hydrogel comprises at least 75% by weight pyrogen-free water.

12. The method according to claim 1, wherein the hydrogel comprises at least 90% by weight pyrogen-free water or saline solution.

13. The method according to claim 1, wherein the hydrogel comprises at least 75% by weight saline solution.

14. The method according to claim 1, wherein the hydrogel has a complex viscosity of about 2 to 13 Pa s.

* * * * *